(12) United States Patent
Berman et al.

(10) Patent No.: US 11,766,507 B2
(45) Date of Patent: Sep. 26, 2023

(54) COMPOSITIONS AND USES OF NANOSCALE DIAMOND PARTICLES FOR ARTIFICIAL JOINT

(71) Applicant: UNIVERSITY OF NORTH TEXAS, Denton, TX (US)

(72) Inventors: Diana Berman, Denton, TX (US); Donghui Zhu, Frisco, TX (US); Olga Shenderova, Raleigh, NC (US)

(73) Assignee: University of North Texas, Denton, TX (US)

( * ) Notice: Subject to any disclaimer, the term of this patent is extended or adjusted under 35 U.S.C. 154(b) by 319 days.

(21) Appl. No.: 17/015,246

(22) Filed: Sep. 9, 2020

(65) Prior Publication Data

US 2021/0069379 A1    Mar. 11, 2021

Related U.S. Application Data

(60) Provisional application No. 62/898,323, filed on Sep. 10, 2019.

(51) Int. Cl.

| | |
|---|---|
| *A61L 27/30* | (2006.01) |
| *A61F 2/30* | (2006.01) |
| *A61L 27/50* | (2006.01) |
| *A61B 17/56* | (2006.01) |

(52) U.S. Cl.
CPC .............. *A61L 27/303* (2013.01); *A61F 2/30* (2013.01); *A61L 27/50* (2013.01); *A61B 2017/564* (2013.01); *A61F 2002/30673* (2013.01); *A61L 2400/12* (2013.01); *A61L 2420/02* (2013.01)

(58) Field of Classification Search
CPC .......... A61L 27/08; A61L 27/06; A61L 27/52; A61L 27/303; B82Y 40/00; C01B 32/28; A61K 31/704; C23C 8/20
See application file for complete search history.

(56) References Cited

U.S. PATENT DOCUMENTS

| | | | | |
|---|---|---|---|---|
| 5,399,351 | A  * | 3/1995 | Leshchiner | A61L 27/52 424/428 |
| 2015/0125379 | A1* | 5/2015 | Gangopadhyay | C01B 32/28 423/446 |
| 2020/0017661 | A1* | 1/2020 | Umemoto | B82Y 40/00 |

OTHER PUBLICATIONS

Wu et al. Nanodiamonds for Biological Applications, 2017, Physical Sciences Reviews, pp. 1-17 (Year: 2017).*

* cited by examiner

*Primary Examiner* — Dah-Wei D. Yuan
*Assistant Examiner* — Andrew J Bowman
(74) *Attorney, Agent, or Firm* — Thomas | Horstemeyer, LLP

(57) ABSTRACT

A new insight on the lubrication of artificial joint components is presented. Addition of small amounts of nanoscale diamond particles to an artificial joint promotes a substantial improvement in friction and wear behavior of the artificial joint surfaces. Artificial joint implants are made from a variety of materials ranging from metal alloys to polymers. Suitable methods of applying nanoscale diamond particles to an artificial joint include (i) coating an effective amount of nanoscale diamond particles onto the artificial joint prior to implants; (ii) applying a composition to the artificial joint during an artificial joint implanting surgery, wherein said composition comprises a biocompatible carrier fluid and an effective amount of nanoscale diamond particles dispersed in the biocompatible carrier fluid; (iii) injecting the composition for lubricating the artificial joint into the artificial joint.

19 Claims, 16 Drawing Sheets

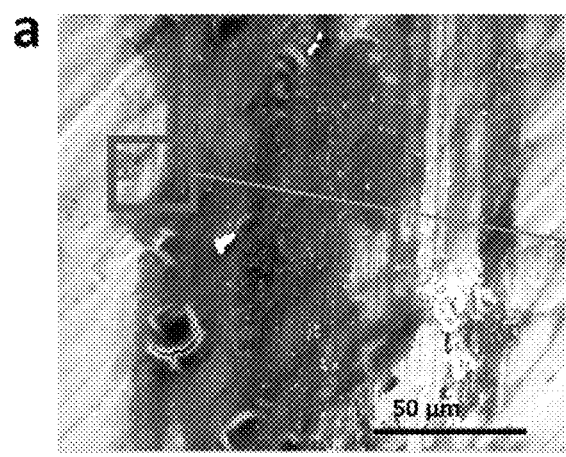
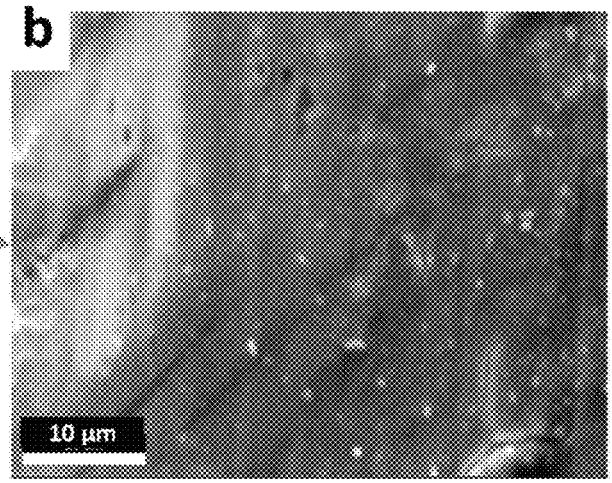
FIG. 5A  FIG. 5B
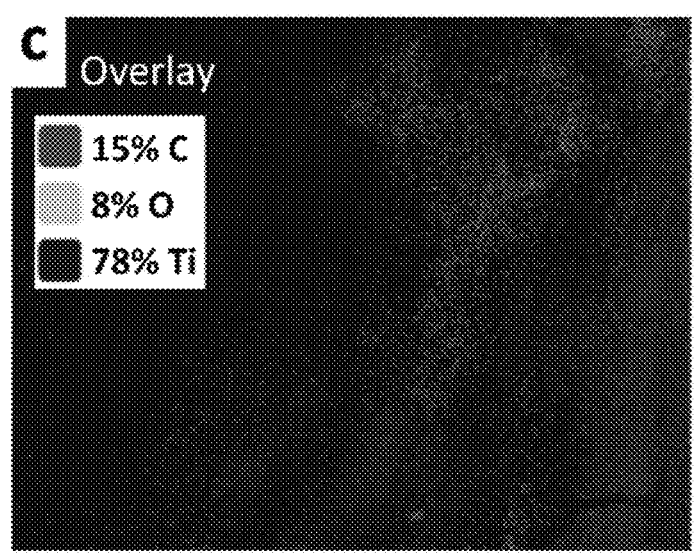
FIG. 5C

COMPOSITIONS AND USES OF NANOSCALE DIAMOND PARTICLES FOR ARTIFICIAL JOINT

RELATED APPLICATION

This application claims the benefit of U.S. Provisional Application Ser. No. 62/898,323, filed Sep. 10, 2019, which is incorporated herein by reference in its entirety.

TECHNICAL FIELD

The present disclosure generally relates to nanoscale diamond particles that are used in artificial joints.

BACKGROUND

Premature natural joint degeneration is a common problem in the population over the age of 40 as a result of excessive loading conditions as well as failure of normal repair processes. Artificial joints made from metal, ceramic, or plastic materials have become the only long-term solution for relief from pain, mobility, or other adverse health effects related to joint degradation and failure. In recent years, the number of orthopaedic surgeries substantially increased, though reliability and lifetime of the artificial joints remain a major issue.

During operation, artificial joints are exposed to a complex environment and subjected to mechanical degradation. Additionally, biocompatibility of the materials, or their ability not to cause an inflammatory or toxic response, is an important aspect to consider.

The search for biocompatible, tribologically efficient materials led to the exploration of different ceramic and metal alloy components. Ideally, the joint replacement material should exhibit an identical performance to the bone when in operation. Ultra-high-molecular-weight polyethylene (UHMWPE) was used in earlier years, but raised concerns with regard to adverse tissue reactions. UHMWPE was replaced with stainless steel and then with Co—Cr—Mo and alumina, which demonstrated good wear resistance but lead to inflammation and pain in long-term. So far, titanium remains the most favorable materials for artificial joints. This has led to extensive research on titanium-based alloys for biomedical applications, such as Ti—Nb—Ta—Zr or TNZT, Ti-6Al-7Nb, Ti-6Al-4V, and Ti-5Al-2.5Fe, among others. Titanium and titanium-based alloys are the preferred materials used for hip cup shells due to their high corrosion resistance and biocompatibility over other materials, such as conventional stainless steels and cobalt-based alloys. However, high wear of the titanium components during exposure to normal and shear stresses is a major cause for their failure. As a result, degradation of the metal implants during movement of the joints limits their lifetime.

SUMMARY

An alternative to modification of the alloy composition is to modify the lubrication media with biocompatible additives. Nanoscale diamond particles (NDs) have proven to be excellent friction and wear modifiers in various sliding systems. Specifically, adding small amounts of nanoscale diamond particles to artificial joints resulted in substantial decrease in friction and wear of joint surfaces. NDs can provide lubrication for artificial joints. In terms of biocompatibility, different forms of carbon were already considered in various in-vivo and in-vitro studies. Previous studies demonstrated biocompatibility of nanoscale diamond particles. Naturally occurring graphitic layers have been detected in metal-on-metal hip replacements. Therefore, nanoscale diamond particles are an ideal solution for improving the longevity of artificial joint components in the body.

Suitable methods of applying nanoscale diamond particles to an artificial joint include (i) coating an effective amount of nanoscale diamond particles onto the artificial joint prior to implant; (ii) applying a composition to the artificial joint during an artificial joint implant surgery, wherein said composition comprises a biocompatible carrier fluid and an effective amount of nanoscale diamond particles dispersed in the biocompatible carrier fluid; (iii) injecting the composition into the artificial joint.

BRIEF DESCRIPTION OF THE DRAWINGS

Further aspects of the present disclosure will be readily appreciated upon review of the detailed description of its various aspects, described below, when taken in conjunction with the accompanying drawings.

FIGS. 5A-5F are a SEM-EDS map of the wear track formed during the test in SBF+0.1 wt. % NDs at 0.5 N load (Hertzian contact pressure ~0.35 GPa). (FIG. 5A) The area of the wear track with (FIG. 5B) higher magnification image is highlighted. (FIG. 5C) Overlay map and detailed (FIG. 5D) carbon, (FIG. 5E) oxygen and (FIG. 5F) titanium map demonstrate uniformity of the titanium and oxygen concentration inside and outside wear track while carbon is found inside the wear track only.

(FIG. 6A) Overview of the wear track selected for the Raman 2D map analysis. (FIG. 6B) Raman spectra inside and outside the wear track for the tests performed in (FIG. 6C) SBF+0.1 wt. % NDs and (FIG. 6C) pure SBF.

(FIG. 8C) *E. coli* growth and adhesion on Ti and Ti-ND plates by SEM; (FIG. 8D) Comparison of numbers of *E. coli* attached to Ti and Ti-ND plates; * indicates p<0.05,  indicates p<0.01, * indicates p<0.001.

DETAILED DESCRIPTION

Figure 1A:
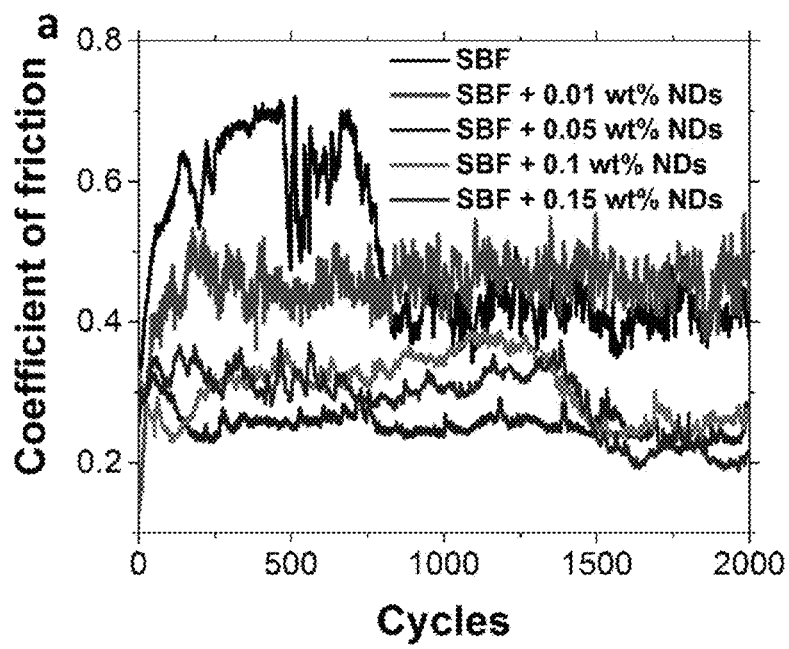
FIG. 1A is a graph of the coefficient of friction values during sliding at 0.25 N load in different concentrations of ND solution in simulated body fluid (SBF).

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Aspects of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some aspects, the term "about" can include traditional rounding according to significant figures of the numerical value. In addition, the phrase "about 'x' to 'y'", where 'x' and 'y' are numerical values, includes "about 'x' to about 'y'".

In some instances, units may be used herein that are non-metric or non-SI units. Such units may be, for instance, in U.S. Customary Measures, e.g., as set forth by the National Institute of Standards and Technology, Department of Commerce, United States of America in publications such as NIST HB 44, NIST HB 133, NIST SP 811, NIST SP 1038, NBS Miscellaneous Publication 214, and the like. The units in U.S. Customary Measures are understood to include equivalent dimensions in metric and other units (e.g., a dimension disclosed as "1 inch" is intended to mean an equivalent dimension of "2.5 cm"; a unit disclosed as "1 pcf" is intended to mean an equivalent dimension of 0.157 $kN/m^3$; or a unit disclosed 100° F. is intended to mean an equivalent dimension of 37.8° C.; and the like) as understood by a person of ordinary skill in the art.

In some aspects, the present disclosure provides a composition for lubricating an artificial joint containing (i) a biocompatible carrier fluid; and (ii) an effective amount of nanoscale diamond particles dispersed in the biocompatible carrier fluid to reduce friction at the artificial joint.

Nanoscale diamond particles are used for friction and wear reduction in artificial joint implants. Addition of small amounts of nanoscale diamond particles to a biocompatible carrier fluid has a substantial reduction in friction and wear of the surfaces.

In one or more aspects, the nanoscale diamond particles on its own, as well as when dissolved or dispersed in a biocompatible carrier fluid, are effective to reduce coefficient of friction by at least 50% as compared to the otherwise same composition except without the nanoscale diamond particles.

In one or more aspects, the nanoscale diamond particles on its own, as well as when dissolved or dispersed in a biocompatible carrier fluid, are effective to reduce wear by at least one order of magnitude as compared to the otherwise same composition except without the nanoscale diamond particles.

In one or more aspects, the nanoscale diamond particles on its own, as well as when dissolved or dispersed in a biocompatible carrier fluid, are effective to reduce bacteria growth by at least 20% as compared to the otherwise same composition except without the nanoscale diamond particles.

In one embodiment, the physical shape of the nanoscale diamond particles can be spherical, elliptical, faceted, or a mixture thereof. In another embodiment, and the nanoscale diamond particles have a volumetric size of about 1 nm to about 20 nm, about 1 nm to about 10 nm, about 2 nm to about 10 nm, about 2 nm to about 8 nm, about 2 nm to about 6 nm, about 3 nm to about 5 nm, about 3 nm, about 4 nm, about 5 nm, about 6 nm, about 7 nm, about 9 nm or about 10 nm.

The nanoscale diamond particles may be carboxylated, which is referred to the surface-modification of nanoscale diamond particles with carboxylate functionality. This functionality can be achieved by oxidation reaction of nanoscale diamond particles with acids such as sulfuric acid and nitric acid.

Carbon atoms in the nanoscale diamond particles are primarily $sp^3$ hybridized. Carbons with $sp^2$ hybridized orbitals are considered defects in nanodiamond since all carbon atoms should have $sp^3$ hybridized orbitals in a pure nanodiamond structure. The term "orbital hybridization", as used herein, refers to the type of hybrid orbitals of the carbon atoms which make of the nanodiamond structure. In practice, X-ray diffraction (XRD) can be used to estimate or characterize the hybridization of carbon, where $sp^3$ carbon has a diamond-like x-ray fingerprint and $sp^2$ carbon has a graphite-like x-ray fingerprint.

In one embodiment, the nanoscale diamond particles include carbon atoms, wherein the carbon atoms have an orbital hybridization that is about 50% to about 99% $sp^3$ carbon, about 60% to about 99% $sp^3$ carbon, about 70% to about 99% $sp^3$ carbon, about 80% to about 99% $spa^3$ carbon, about 90% to about 99% $sp^3$ carbon, or about 95% to about 99% $sp^3$ carbon.

Nanoscale diamond particles can be synthesized by a variety of processes, including detonation technique, laser ablation, high-energy ball milling of high-pressure high-temperature (HPHT) diamond microcrystals, plasma-assisted chemical vapor deposition (CVD), autoclave synthesis from supercritical fluids, chlorination of carbides, ion irradiation of graphite, electron irradiation of carbon 'onions', ultrasound cavitation, and a combination thereof.

In one or more aspects, nanoscale diamond particles are dissolved or dispersed in a biocompatible carrier fluid, which is selected from the group consisting of a simulated body fluid, a synovial fluid, a combination of both. One or more additional fluids can be added to the biocompatible carrier fluid to improve its functional property.

Nanoscale diamond particles on its own, as well as when dissolved or dispersed in a biocompatible carrier fluid, can be applied in an artificial joint. The artificial joint is made of titanium-based alloys, ultra-high-molecular-weight polyethylene, high-density polyethylene, polytetrafluoroethylene, polyoxymethylene, stainless steel, cobalt-based alloys, chromium-based alloys, molybdenum-based alloys, or a combination thereof.

In one or more aspects, nanoscale diamond particles can be used to lubricate artificial joints made of titanium based alloys. Some of these alloys include Ti—Nb—Ta—Zr, Ti-6Al-7Nb, Ti-6Al-4V, Ti-5Al-2.5Fe, or a combination thereof.

In one or more other aspects, the concentration of the nanoscale diamond particles in the biocompatible carrier fluid is about 0.001 wt % to about 0.25 wt %, 0.005 wt % to about 0.25 wt %, about 0.01 wt % to about 0.25 wt %, about 0.01 wt % to about 0.2 wt %, about 0.05 wt % to about 0.2 wt %, about 0.05 wt % to about 0.15 wt %, about 0.1 wt % to about 0.15 wt %, about 0.05 wt %, about 0.1 wt %, or about 0.15 wt % based upon a weight of the composition.

In one or more other aspects, artificial joints refers to implanted joints that replace hip joints, joints of hand, elbow joints, wrist joints, glenohumeral joint, acromioclavicular joint, sternoclavicular joints, vertebral articulations, temporomandibular joints, sacroiliac joints, knee joints, or articulations of foot.

In one or more aspects, nanoscale diamond particles can be applied to artificial joints for mammals. More specifically they are preferably used in humans as well as for veterinary purposes.

A variety of methods for applying nanoscale diamond particles into artificial are provided. In one embodiment, the method includes coating an effective amount of nanoscale diamond particles onto the artificial joint prior to implant. In another embodiment, the method includes applying a composition disclosed herein into the artificial joint during an artificial joint implanting surgery, wherein the composition comprises a biocompatible carrier fluid and an effective amount of nanoscale diamond particles dispersed in the biocompatible carrier fluid. In another embodiment, the method includes injecting the composition disclosed herein into the artificial joint.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in aspects of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "volumetric size", as used herein, refers to the size of the nanoscale diamond particles. In practice, the volumetric size of nanoscale diamond particles can be estimated or characterized by dynamic light scattering. DLS volumetric sizes are reported as a % composition of the total volume with particles having a given range of diameters.

The term "coefficient of friction", as used herein, refers to a value that corresponds to the relationship between friction forces of two objects. The friction force is a force exerted by a surface when an object moves across it, or makes an effort to move across it.

The term "biocompatible", as used herein, may refer to the ability of the material to perform its intended function, with the desired degree of incorporation in the host, without eliciting any undesirable local or systemic effects in that host.

The term "hertzian contact pressure", as used herein, refers to the localized stress pressure that develops as two curved surfaces come in contact and deform slightly under imposed loads. This amount of deformation is dependent on the modulus of elasticity of the materials in contact. It gives the contact stress as a function of the normal contact force, the radii of curvature of both bodies and the modulus of elasticity of both bodies. Hertzian contact stress pressure forms the foundation for the equations for load bearing capabilities and fatigue life in bearings, gears, and any other bodies where two surfaces are in contact.

As used herein, "about," "approximately," and the like, when used in connection with a numerical variable, generally refers to the value of the variable and to all values of the variable that are within the experimental error (e.g., within the 95% confidence interval for the mean) or within +1-10% of the indicated value, whichever is greater.

As used herein, "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

Reference throughout this specification to "one embodiment", "an embodiment", "another embodiment", "some embodiment," means that a particular feature, structure or characteristic described in connection with the embodiment is included in at least one embodiment of the present invention. Thus, appearances of the phrases "in one embodiment," "in an embodiment," "in another embodiment", or "in some embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Liquid Formulations

Liquid formulations contain an effective amount of nanoscale diamond particles, possibly with one or more additional active agents, dissolved or suspended in a biocompatible carrier fluid.

Suitable carrier fluids include, but are not limited to simulated body fluid, distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or a human.

Preferably, liquid formulations are isotonic relative to physiological fluids and of approximately the same pH, ranging e.g., from about pH 4.0 to about pH 7.4, more preferably from about pH 6.0 to pH 7.0. The carrier fluid can include one or more physiologically compatible buffers, such as a phosphate buffers. One skilled in the art can readily determine a suitable saline content and pH for an aqueous solution for administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

Liquid formulations may also contain minor amounts of polymers, surfactants, or other excipients well known to those of the art.

EXAMPLES

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of aspects of the present disclosure.

To reproduce the joint environment in the body, tribological testing was performed in a simulated body fluid. SBF was prepared using a standard protocol. Sodium chloride, sodium bicarbonate, potassium chloride, potassium phosphate dibasic trihydrate, magnesium chloride hexahydrate, calcium chloride dihydrate, and sodium sulfate were dissolved in the right proportion in distilled water and held in an incubator at a constant temperature of 37° C. The solutions were used within a week to avoid any agglomeration and degradation of the mixture. The fresh solution was prepared for replicate tests.

Grade 5 purity (99.999% titanium) titanium balls (diameter 6 mm) and titanium flats (RMS roughness measured with Veeco Dektak 150 Surface Profiler Rq=50-60 nm) were used during testing. The hardness of the balls and flats measured with a Shimadzu Microhardness Tester were 4900 MPa and 3300 MPa, correspondingly. Tests were performed using the Anton Paar pin-on-disk macroscale tribometer in reciprocating mode. The length of the wear track was kept at 5 mm with reciprocal motion at 1 Hz. The samples were immersed in simulated body fluid during the tests and the temperature was kept at 37° C. to approximate conditions inside the body a closely as possible. During the tests, the applied load was varied from 0.25 N up to 1 N (maximum Hertzian contact pressure of 0.28-0.45 GPa). The contact pressures experienced by the surfaces during sliding were selected based on the previously reported contact pressure values for hip replacement contacts.

Small amounts of carboxylated detonation nanoscale diamond particles with 5 nm average volumetric size and zeta potential of −35 mV dispersed in DI water at 10 mg/mL were introduced directly to the simulated body fluid and the resulting solution was sonicated for at least 30 minutes. The added amounts of 1, 5, 10, 15, and 20 vol. % of the nanodiamond solution (NDS) correspond to 0.01, 0.05, 0.1, 0.15, and 0.2 wt % concentrations of nanoscale diamond particles in SBF, correspondingly. To confirm reproducibility of the results, at least three replicate tribotests were performed for each concentration of nanoscale diamond particles in SBF.

After tests, the simulated body fluid was removed and the samples were rinsed using DI water and the wear tracks were further analyzed. Optical images of the wear tracks were acquired using a Zeiss Optical Microscope. Raman analysis was performed Nicolet Almega XR Dispersive Raman spectrometer with 532 nm green laser. The samples were further characterized using an FEI Quanta 200 Scanning Electron Microscope (SEM) with energy dispersion x-ray analysis (EDX) to analyze the surface modification changes in the wear track.

To estimate the wear rate after the tests, the wear volume of the ball side is calculated as follows:

$$V = \left(\frac{\pi h}{6}\right)\left(\frac{3d^2}{4} + h^2\right) \quad (1)$$

where d is the wear scar diameter, r is the radius of the ball, and h is the wear scar depth:

$$V = \left(\frac{\pi h}{6}\right)\left(\frac{3d^2}{4} + h^2\right) \quad (2)$$

Figure 1B:
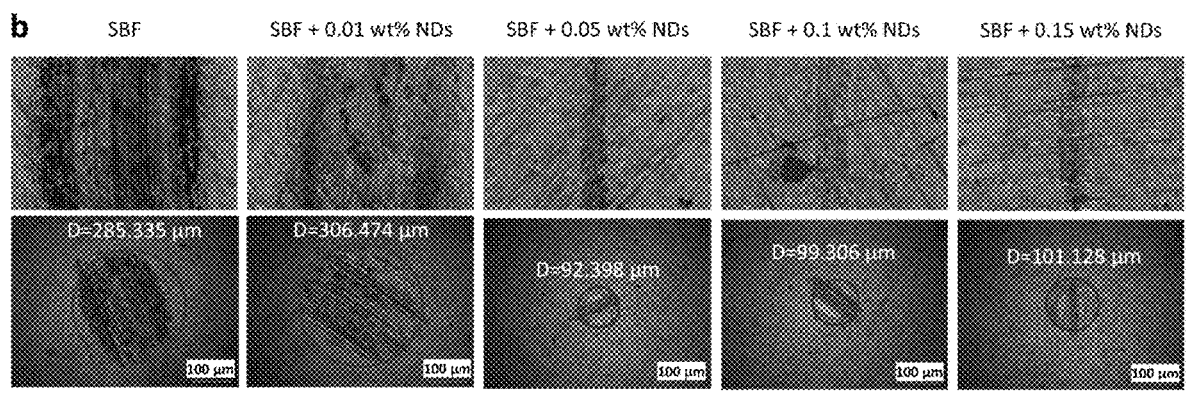
FIG. 1B is a picture of the wear tracks formed during sliding at 0.25 N load in different concentrations of ND solution in SBF.

Changes in the coefficient of friction (COF) and wear values of the titanium surfaces were monitored during sliding under 0.25 N applied load. The results demonstrate that in contrast to pure SBF, the addition of 0.05 wt % of the nanodiamond leads to a two times reduction of the COF value. As demonstrated in FIG. 1A-B, 0.01 wt % shows almost negligible changes. Therefore, further analyses focused on 0.05, 0.1, and 0.15 wt. % concentrations.

Figure 2A:
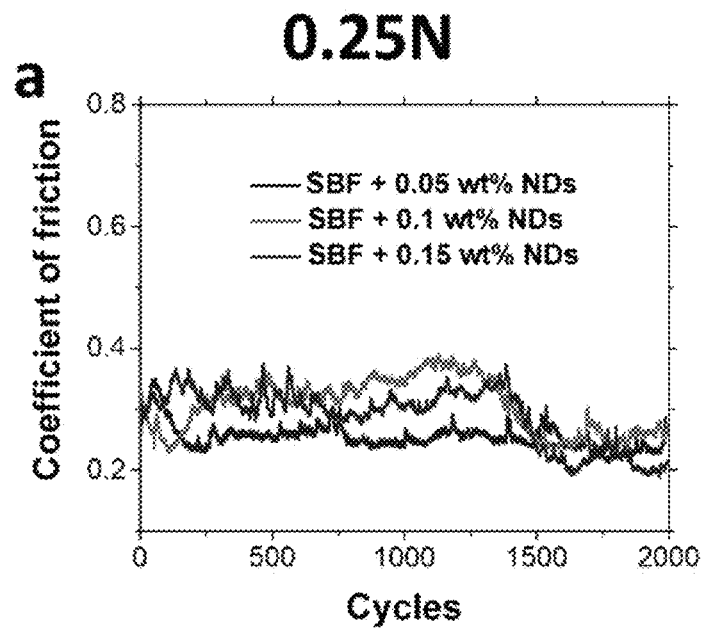
FIG. 2A is a graph of the coefficient of friction values during sliding in different concentration of ND in SBF under 0.25 N applied load.
Figure 2B:
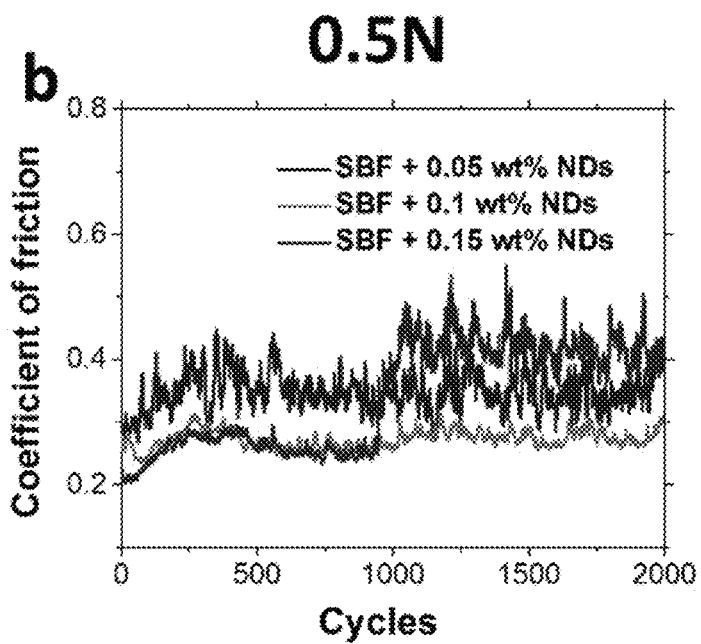
FIG. 2B is a graph of the coefficient of friction values during sliding in different concentration of ND in SBF under 0.5 N applied load.
Figure 2C:
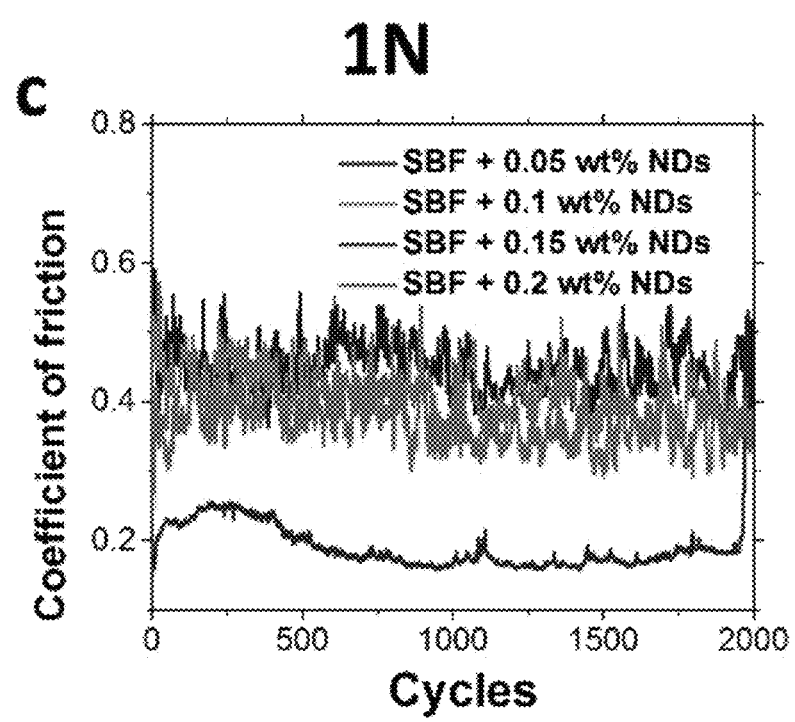
FIG. 2C is a graph of the coefficient of friction values during sliding in different concentration of ND in SBF under 1 N applied load.

Increasing the applied load necessitates an increase in the amount of nanodiamond for enhanced performance. As demonstrated in FIG. 2, 0.1 wt. % works better at 0.5 N applied load, while 0.15 wt. % is optimal for 1 N applied load. This behavior is attributed to higher contact loads requiring a more uniform ND tribolayer, which may be achieved with higher ND content.

Figure 3A:
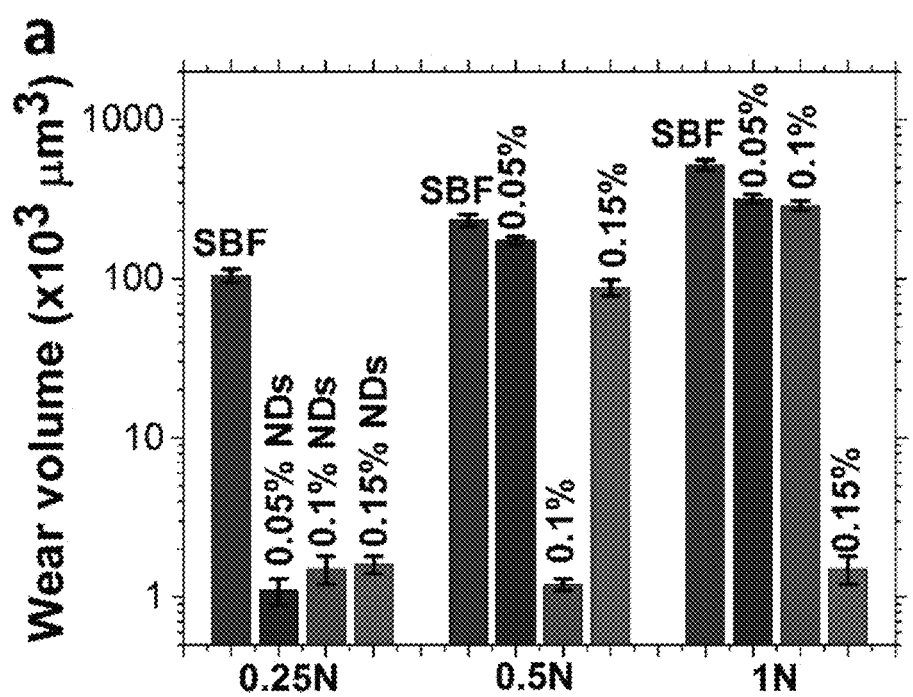
FIG. 3A is a graph of the wear of the titanium surfaces during the tests at different loads. At 0.25 N load (Hertzian contact pressure ~0.28 GPa), the minimum wear is observed for 0.05 wt % of NDs; at 0.5 N load (Hertzian contact pressure ~0.35 GPa), the minimum wear is for 0.1 wt. % NDs; and at 1 N load (Hertzian contact pressure ~0.45 GPa), the minimum wear is for 0.15 wt. % NDs.
Figure 3B:
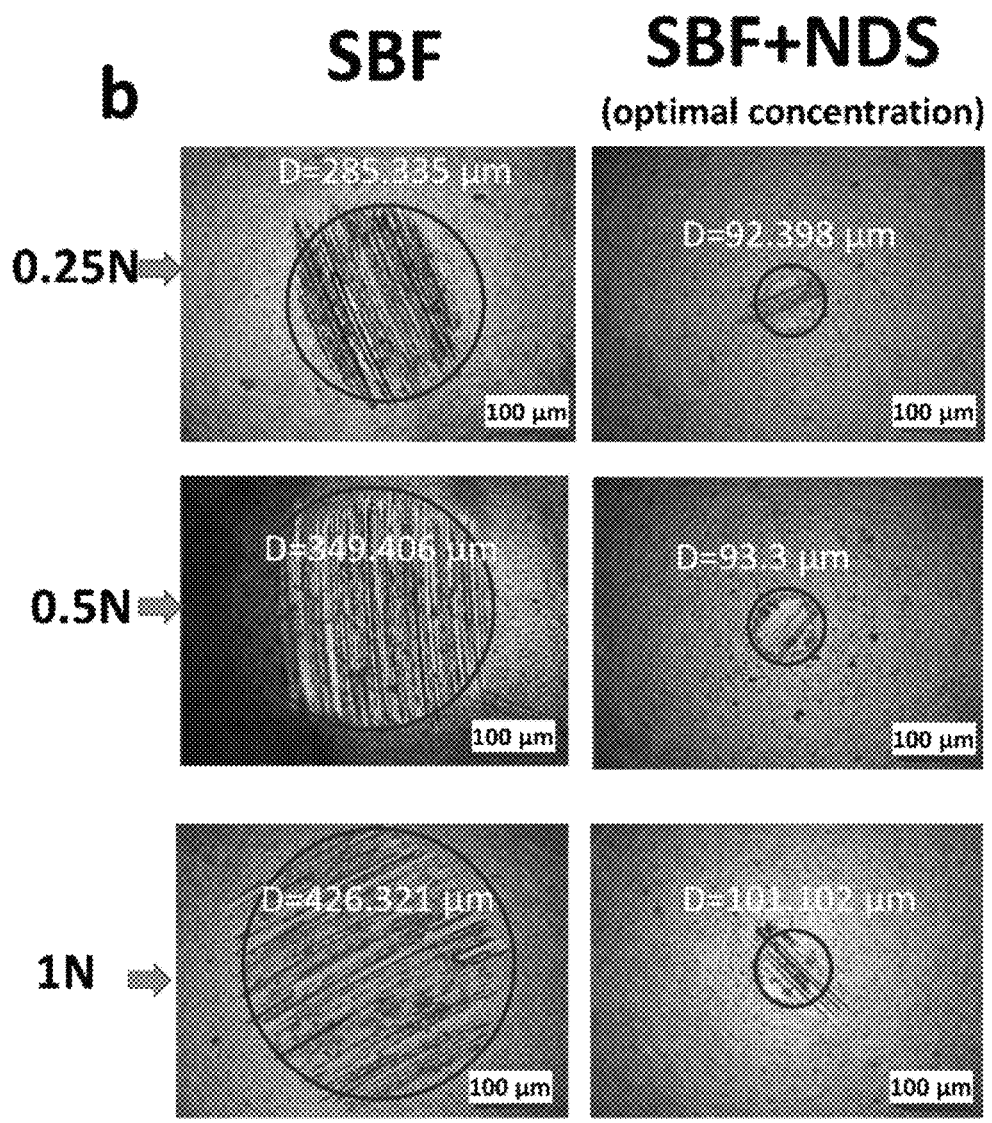
FIG. 3B is optical images of the ball wear scar for the pure SBF and SBF with optimal concentrations of NDs.

Analysis of the wear tracks further supports the benefits of different ND concentrations for each specific applied load (FIG. 3). Nevertheless, on average, the presence of NDs in SBF resulted in lower wear than for the SBF alone, and the resulting wear of the titanium surfaces depends on both parameters: ND concentration and applied load. FIG. 3 highlights the wear scar measurements for the optimal concentrations of NDs at each load.

Further understanding of the mechanism of lubrication improvement in the presence of NDs is possible through detailed characterization of the wear tracks corresponding to the tests in pure SBF and in SBF with an optimal concentration of NDs.

Figure 4A:
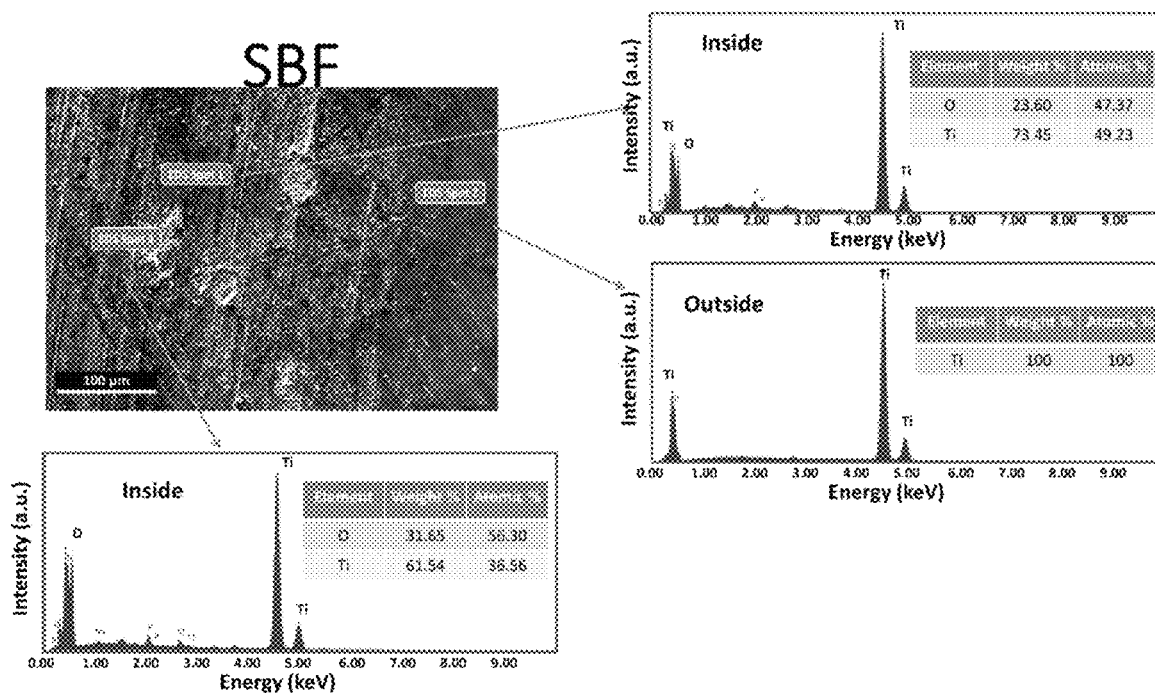
FIG. 4A is a SEM-EDS analysis of the wear track formed during the tests in SBF at 0.5 N load (Hertzian contact pressure ~0.35 GPa). Analysis indicates a high concentration of oxygen inside the wear track. The Na, F, and Cl peaks originate from the residue of the SBF on the surface and are intentionally excluded from the further analysis of the oxidation amount.
Figure 4B:
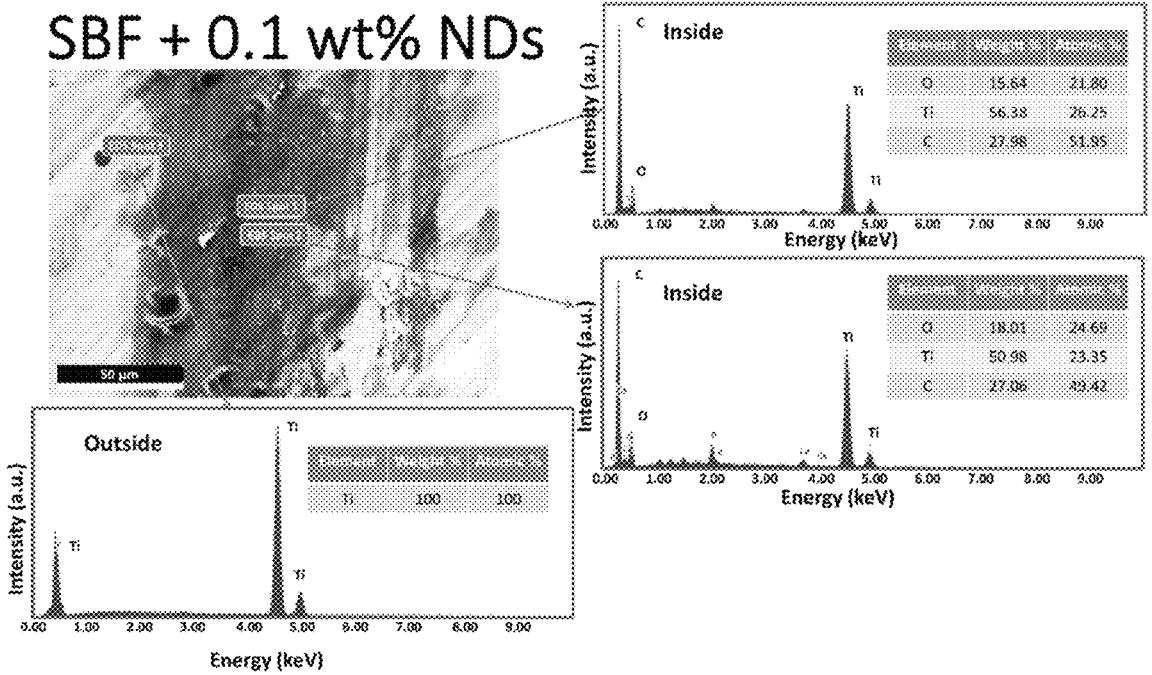
FIG. 4B is a SEM-EDS analysis of the wear track formed during the tests in SBF+0.1 wt. % NDs at 0.5 N load (Hertzian contact pressure ~0.35 GPa). Inside the wear track, the presence of carbon is observed. The Na, F, and Cl peaks originate from the residue of the SBF on the surface and are intentionally excluded from the further analysis of the oxidation amount.
Figure 5D:
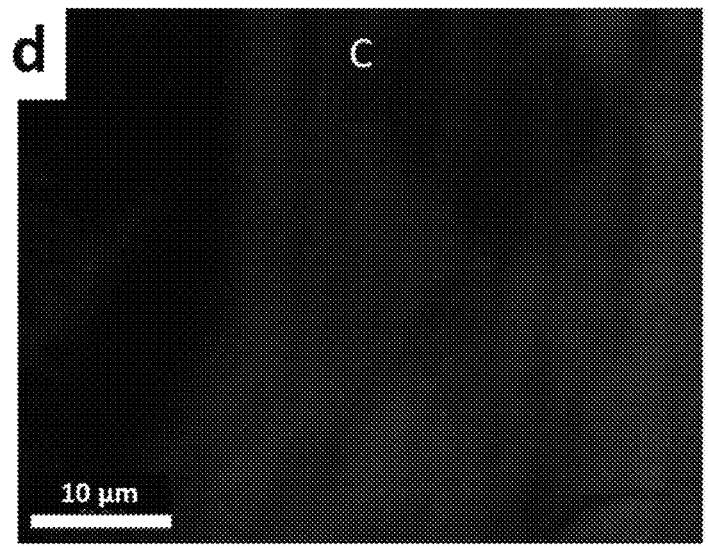
Figure 5E:
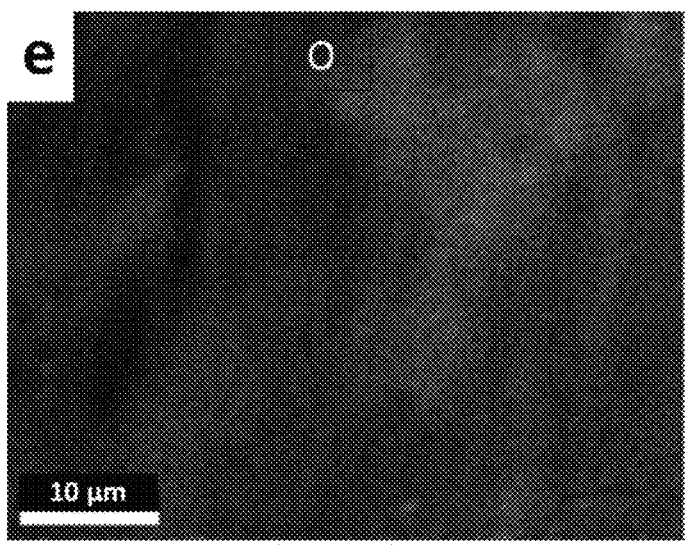
Figure 5F:
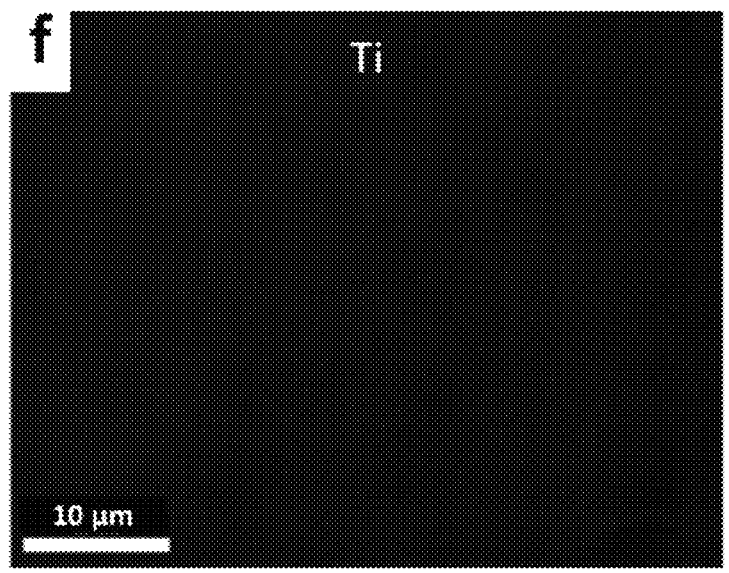
Figure 6A:
FIGS. 6A-6D are a Raman 2D map of the $sp^3$ bonded carbon peak (at ~1330 cm-1) of the wear track formed during the test with SBF+0.1 wt. % NDs at 0.5 N load (Hertzian contact pressure 0.35 GPa).
Figure 6B:
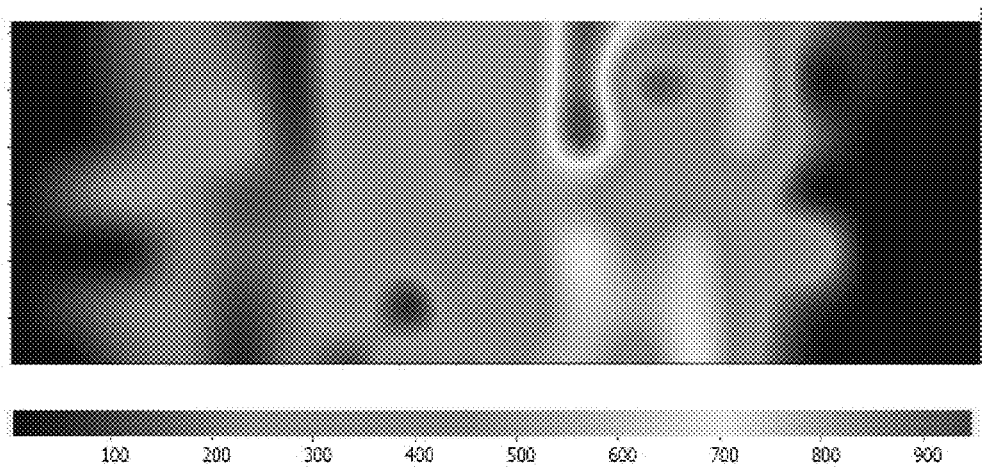
Figure 6C:
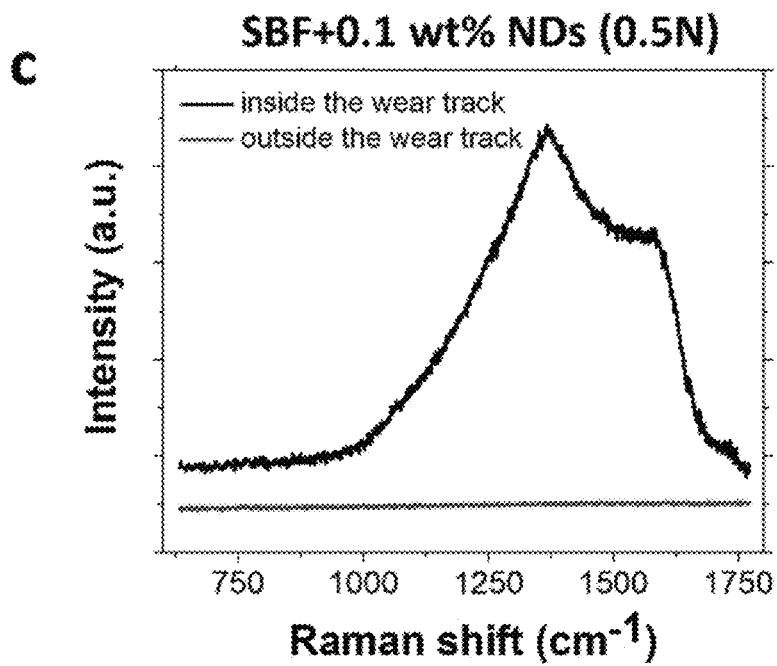
Figure 6D:
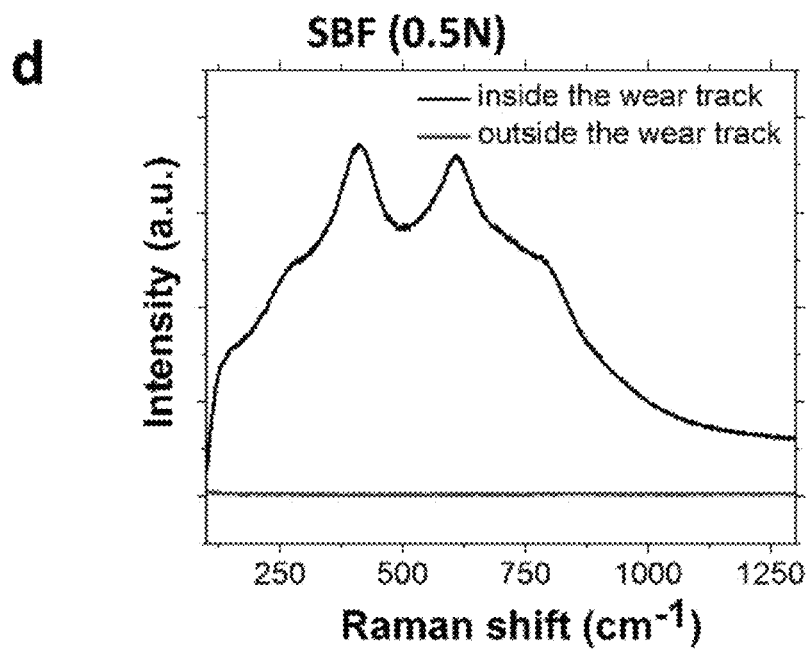

Analysis of the tracks formed during the sliding in pure SBF (FIG. 4) and SBF with 0.1 wt. % NDs at 0.5 N load (FIG. 5) was performed by acquiring energy dispersive x-ray spectroscopy (EDS) spectra from multiple points inside and outside of the wear tracks. The tests indicate that for the pure SBF, titanium oxide is dominant within the wear track. In the case of pure SBF, the titanium surfaces are exposed to sliding contact and their wear increases oxidation of the wear track region. When NDs are introduced to the SBF, the wear track oxidation is substantially lower. Interestingly, the EDS spectra inside the wear track clearly indicate the presence of carbon. Therefore, formation of the carbon rich layer in the wear track provides better tribological performance of the sliding system and protects the underlying titanium substrate from extensive wear. Similar wear and corrosion protection characteristics of carbon films were observed in case of graphitic layers. As a result, less titanium surface is exposed to the oxidation in SBF environment rich of corrosion promoting ions.

Further evaluation of the uniformity of the carbon coverage inside the wear track formed during sliding in the SBF+0.1 wt. % NDs is shown in FIGS. 6A-6D. A detailed EDS map of the SBF+0.1 wt. % NDs wear track (FIG. 6D) indicates uniformity of the carbon presence inside the wear track. Higher concentrations of oxygen correlates with regions of lower carbon presence. Thus, the presence of carbon plays a critical role in reducing oxidation and minimizing wear of the sliding surfaces.

Figure 7A:
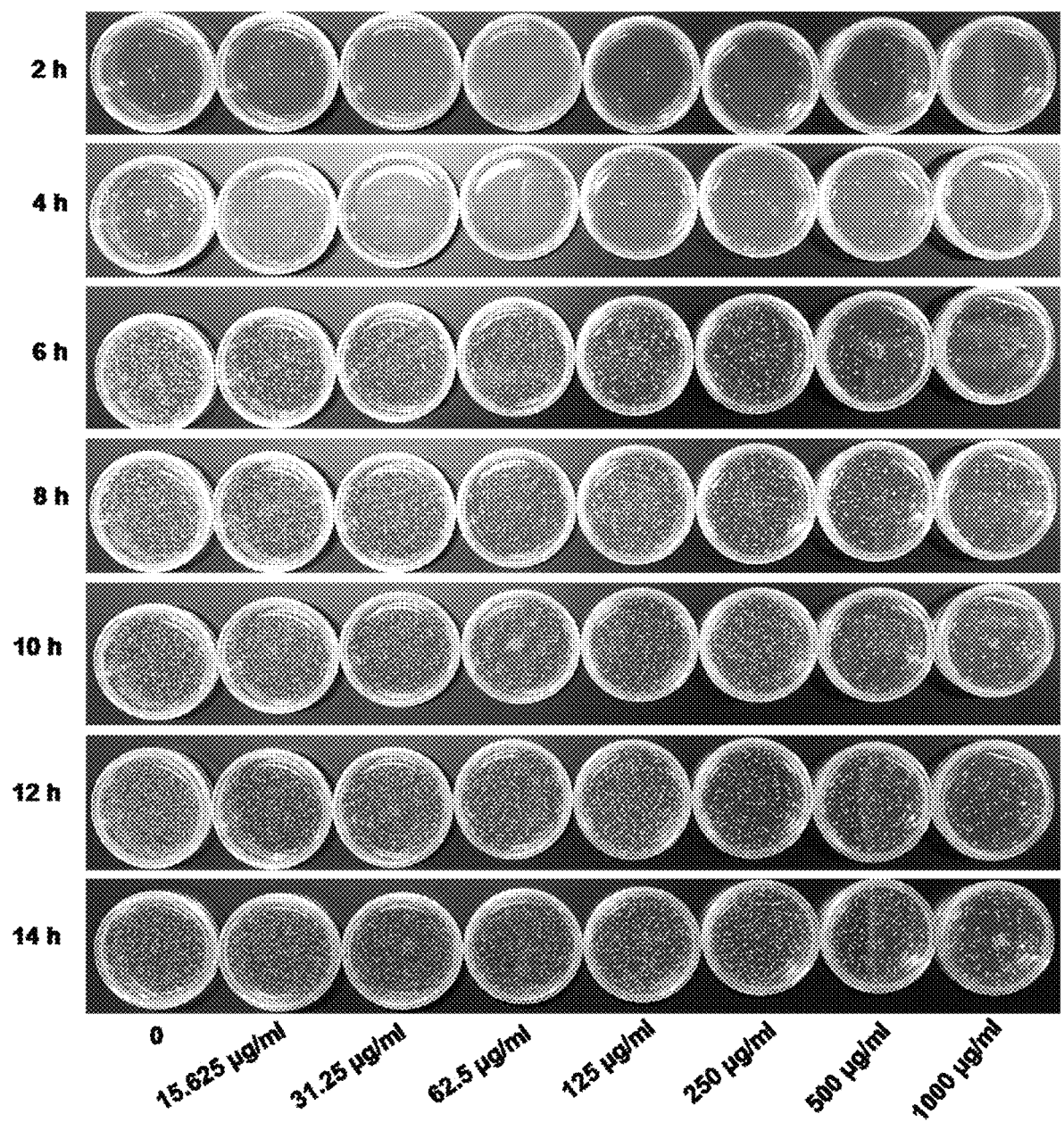
FIG. 7A is pictures of colony formation assay of *S. aureus* treated with ND.
Figure 7B:
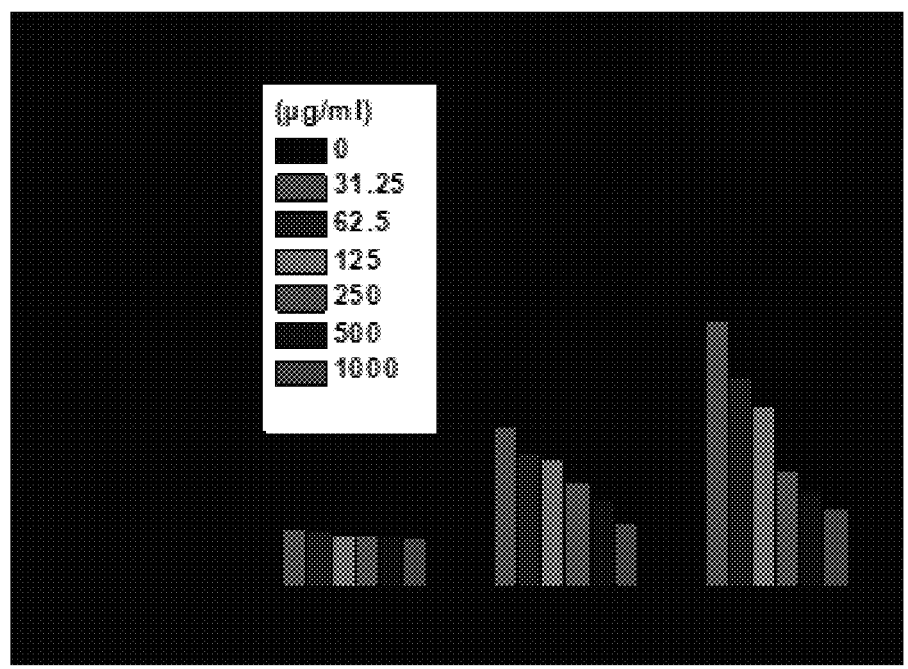
FIG. 7B is a graph of colony formation assay of *S. aureus* treated with ND.
Figure 8A:
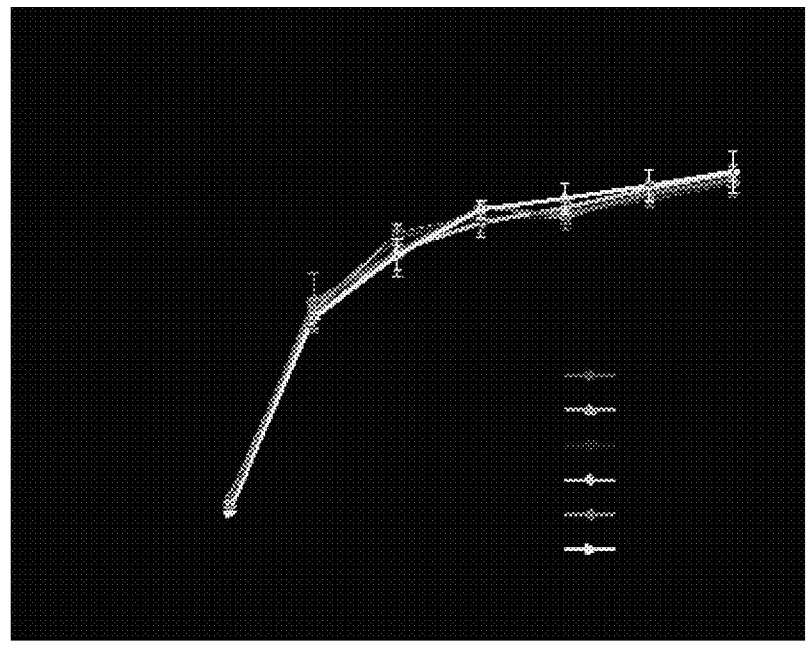
FIGS. 8A-8D display the antibacterial activity of ND on *E. coli*. Bacteria growth curve treated with different concentration of ND (FIG. 8A) and ND-BSA (FIG. 8B)
Figure 8B:
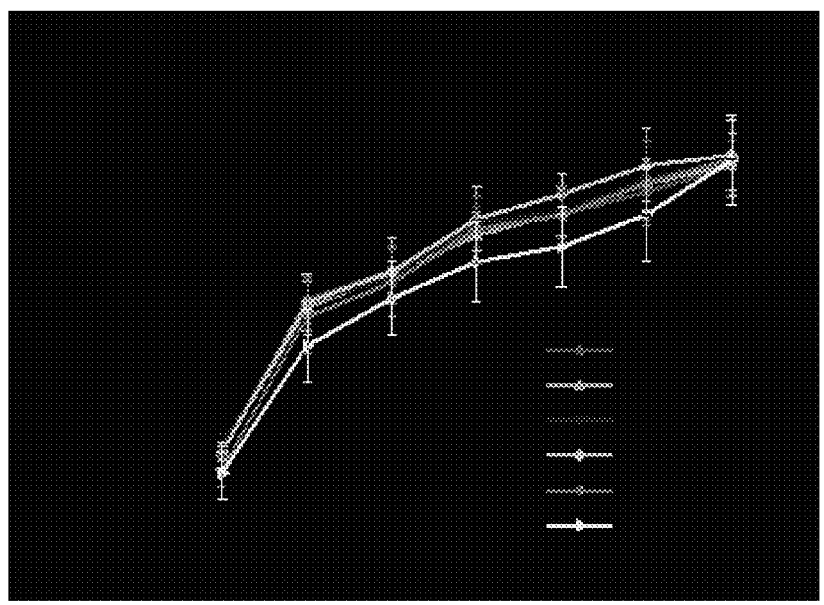
Figure 8C:
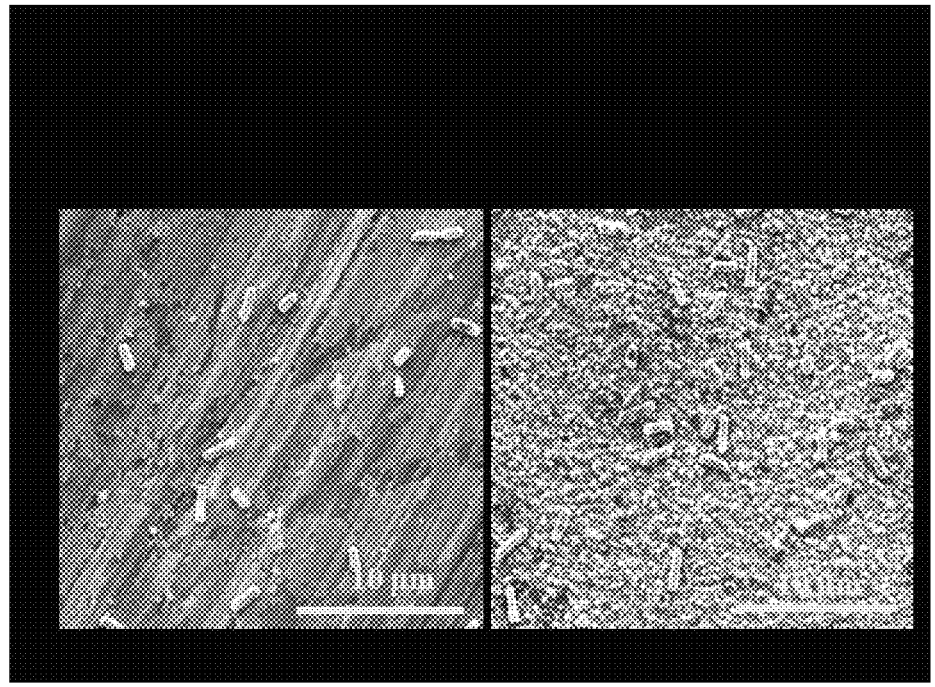
Figure 8D:
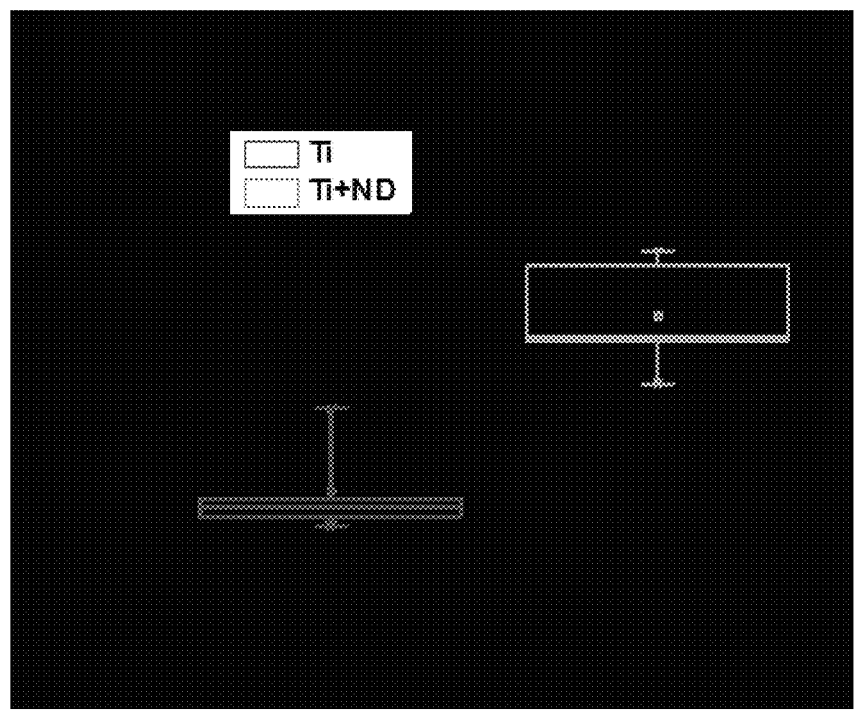

For *S. aureus* exposed to ND (FIG. 8A), the OD showed a concentration-dependent decrease. Consist with the result of the growth curve, the number of colonies was largely reduced compared with the control group (FIG. 7A-B). However, it was shown that the increase in OD of *E. coli* cultures exposed to ND was little influenced by a broad range of ND concentrations, in contrast to what has been observed for *S. aureus*. When exposed to ND-BA, the growth curve followed a similar trend for both *S. aureus* (FIG. 8B) and *E. coli*. To further investigate the antibacterial activity, SEM visualization conducted to evaluate the adhesion on Ti and Ti-UNCD plates. For *S. aureus* (FIG. 8C-D), a single layer of bacterial cells was generally observed, with a higher density of bacterial cells tightly settled on the Ti plate compared with Ti-UNCD plate, whereas much more bacterial cells attached on the Ti-UNCD plate for *E. coli*. Both visual observations and the quantitative bacterial cell count evaluation showed that the extent of bactericidal ability varied considerably among the tested microorganisms.

Figure 9:
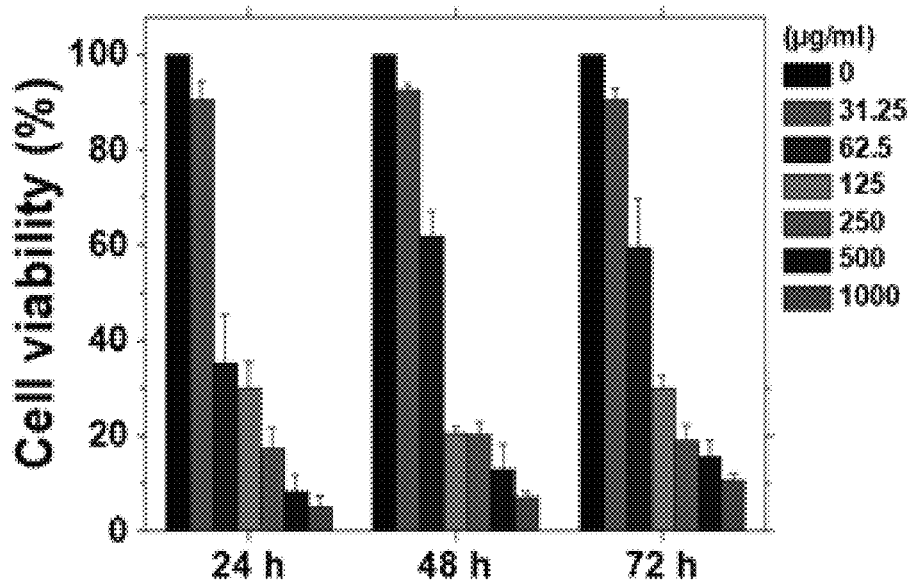
FIG. 9 is a graph of the effects of NDs on cell viability. Effects of ND-BA on cell viability. MC3T3-E1 cells were treated with different concentration of NDs and incubated for 3 days after treatment. 3-(4,5-dimethylthiazol2-yl)-2,5-diphenyltetrazolium bromide) (MTT) was performed to measure cell viability.

To investigate the influence of ND coating on cell morphology and cytoskeletal of MC3T3-E1 cells, fluorescence microscopy images were obtained. MTT was used to screen for any cytotoxic effect caused by ND/ND-PBS+10% Albumin (ND-BA). In case of ND, cells exhibited a significant reduction in viable cell numbers at a concentration of 62.5 µg/ml, whereas the cell cytotoxicity levels were not significantly different when treated with ND-BA even if at a higher concentration up to 1800 µg/ml (FIG. 9). It is obvious that ND-BA particles showed improved viability compared to ND.

Figure 10:
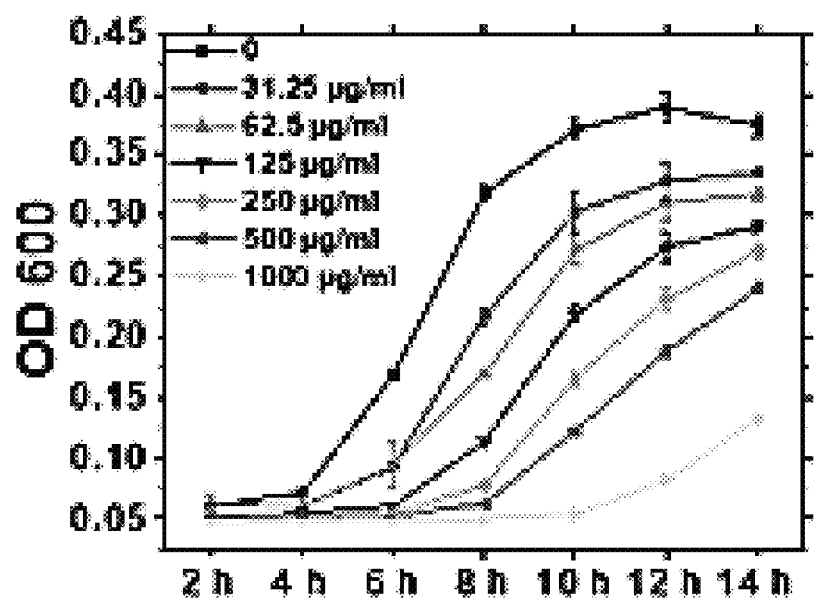
FIG. 10 is a graph of the optical density (OD) measurements of bacteria at a wavelength of 600 nm (OD 600 nm) for *S. aureus*. *S. aureus* was incubated with different concentration of NDs for 16 hours and bacteria growth was measured at OD 600 nm.

For *S. aureus* exposed to ND (FIG. 10), the OD showed a concentration-dependent decrease. Consist with the result of the growth curve, the number of colonies was largely reduced compared with the control group.

The present disclosure further includes the following embodiments.

1A. A composition for lubricating an artificial joint in a subject in need thereof; the composition comprising:
 (i) a biocompatible carrier fluid; and
 (ii) an effective amount of nanoscale diamond particles dispersed in the biocompatible carrier fluid to lubricate the artificial joint when applied to the artificial joint in the subject.

2A. The composition according to paragraph 1A, wherein nanoscale diamond particles are spherical, elliptical, faceted, or a mixture thereof.

3A. The composition according to any one of paragraphs 1A-2A, wherein the nanoscale diamond particles comprise carbon atoms, and Wherein the carbon atoms have an orbital hybridization that is about 50% to about 99% sp3 carbon, about 60% to about 99% sp3 carbon, about 70% to about 99% sp3 carbon, about 80% to about 99% sp3 carbon, about 90% to about 99% sp3 carbon, or about 95% to about 99% sp3 carbon.

4A. The composition according to any one of paragraphs 1A-3A, wherein the nanoscale diamond particles are made by a process selected from the group consisting of detonation technique, laser ablation, high-energy ball milling of high-pressure high-temperature (HPHT) diamond microcrystals, plasma-assisted chemical vapor deposition (CVD), autoclave synthesis from supercritical fluids, chlorination of carbides, ion irradiation of graphite, electron irradiation of carbon 'onions', and ultrasound cavitation, and a combination thereof.

5A. The composition according to any one of paragraphs 1A-4A, wherein the nanoscale diamond particles have a volumetric size of about 1 nm to about 20 nm, about 1 nm to about 10 nm, about 2 nm to about 10 nm, about 2 nm to about 8 nm, about 2 nm to about 6 nm, about 3 nm to about 5 nm, about 3 nm, about 4 nm, or about 5 nm.

6A. The composition according to any one of paragraphs 1A-5A, wherein the nanoscale diamond particles are carboxylated.

7A. The composition according to any one of paragraphs 1A-6A, wherein the nanoscale diamond particles are present at a concentration of about 0.001 wt % to about 0.25 wt %, 0.005 wt % to about 0.25 wt %, about 0.01 wt % to about 0.25 wt %, about 0.01 wt % to about 0.2 wt %, about 0.05 wt % to about 0.2 wt %, about 0.05 wt % to about 0.15 wt %, about 0.1 wt % to about 0.15 wt %, about 0.05 wt %, about 0.1 wt %, or about 0.15 wt % based upon an entire weight of the composition.

8A. The composition according to any one of paragraphs 1A-7A, wherein the biocompatible carrier fluid is selected from the group consisting of a simulated body fluid, a synovial fluid, a combination thereof, and mixtures thereof with one or more additional fluids.

9A. The composition according to any one of paragraphs 1A-8A, wherein the composition is effective to reduce coefficient of friction at the artificial joint by at least 50% as compared to the otherwise same composition except without the nanoscale diamond particles.

10A. The composition according to any one of paragraphs 1A-9A, wherein the composition is effective to reduce wear at the artificial joint by at least one order of magnitude as compared to the otherwise same composition except without the nanoscale diamond particles.

11A. The composition according to any one of paragraphs 1A-10A, wherein the composition is effective to reduce bacteria growth by at least 20% as compared to the otherwise same composition except without the nanoscale diamond particles.

12A. The composition according to any one of paragraphs 1A-11A, wherein the artificial joint is made of a material selected from the group consisting of titanium-based alloys, ultra-high-molecular-weight polyethylene, high-density polyethylene, polytetrafluoroethylene, polyoxymethylene, stainless steel, cobalt-based alloys, chromium-based alloys, molybdenum-based alloys, and a combination thereof.

13A. The composition according to any one of paragraphs 1A-12A, wherein the artificial joint is made of a material selected from the group consisting of Ti—Nb—Ta—Zr, Ti-6Al-7Nb, Ti-6Al-4V, Ti-5Al-2.5Fe, and a combination thereof.

14A. The composition according to any one of paragraphs 1A-13A, wherein the subject is a mammal.

15A. The composition according to any one of paragraphs 1A-14A, wherein the artificial joint is selected from the group consisting of hip joint, joint of hand, elbow joint, wrist joint, glenohumeral joint, acromioclavicular joint, sternoclavicular joint, vertebral articulation, temporomandibular joint, sacroiliac joint, knee joint, articulation of foot, and a combination thereof.

16A. A method of lubricating an artificial joint in a subject in need thereof, the method comprising: coating an effective amount of nanoscale diamond particles onto the artificial joint to lubricate the artificial joint and/or applying an effective amount of a composition according to any one of paragraphs 1A-15A.

17A. The method according to paragraph 16A, wherein nanoscale diamond particles are spherical, elliptical, faceted, or a mixture thereof.

18A. The method according to any one of paragraphs 16A-17A, wherein the nanoscale diamond particles comprise carbon atoms, and wherein the carbon atoms have an orbital hybridization that is about 50% to about 99% sp3 carbon, about 60% to about 99% sp3 carbon, about 70% to about 99% sp3 carbon, about 80% to about 99% sp3 carbon, about 90% to about 99% sp3 carbon, or about 95% to about 99% sp3 carbon.

19A. The method according to any one of paragraphs 16A-18A, wherein the nanoscale diamond particles are made by a process selected from the group consisting of detonation technique, laser ablation, high-energy ball milling of high-pressure high-temperature (HPHT) diamond microcrystals, plasma-assisted chemical vapor deposition (CVD), autoclave synthesis from supercritical fluids, chlorination of carbides, ion irradiation of graphite, electron irradiation of carbon 'onions', and ultrasound cavitation, and a combination thereof.

20A. The method according to any one of paragraphs 16A-19A, wherein the nanoscale diamond particles have a volumetric size of about 1 nm to about 20 nm, about 1 nm to about 10 nm, about 2 nm to about 10 nm, about 2 nm to about 8 nm, about 2 nm to about 6 nm, about 3 nm to about 5 nm, about 3 nm, about 4 nm, or about 5 nm.

21A. The method according to any one of paragraphs 16A-20A, wherein the nanoscale diamond particles are carboxylated.

22A. The method according to any one of paragraphs 16A-21A, wherein the composition is effective to reduce coefficient of friction at the artificial joint by at least 50% as compared to the otherwise same composition except without the nanoscale diamond particles.

23A. The method according to any one of paragraphs 16A-22A, wherein the composition is effective to reduce wear at the artificial joint by at least one order of magnitude as compared to the otherwise same composition except without the nanoscale diamond particles.

24A. The method according to any one of paragraphs 16A-23A, wherein the composition is effective to reduce bacteria growth by at least 20% as compared to the otherwise same composition except without the nanoscale diamond particles.

25A. The method according to any one of paragraphs 16A-24A, wherein the artificial joint is made of a material selected from the group consisting of titanium-based alloys, ultra-high-molecular-weight polyethylene, high-density polyethylene, polytetrafluoroethylene, polyoxymethylene, stainless steel, cobalt-based alloys, chromium-based alloys, molybdenum-based alloys, and a combination thereof.

26A. The method according to any one of paragraphs 16A-25A, wherein the artificial joint is made of a material selected from the group consisting of Ti—Nb—Ta—Zr, Ti-6Al-7Nb, Ti-6Al-4V, Ti-5Al-2.5Fe, and a combination thereof.

27A. The method according to any one of paragraphs 16A-26A, wherein the subject is a mammal.

28A. The method according to any one of paragraphs 16A-27A, wherein the artificial joint is selected from the group consisting of hip joint, joint of hand, elbow joint, wrist joint, glenohumeral joint, acromioclavicular joint, sternoclavicular joint, vertebral articulation, temporomandibular joint, sacroiliac joint, knee joint, articulation of foot, and a combination thereof.

29A. The method according to any one of paragraphs 16A-28A, wherein the nanoscale diamond particles and/or the composition are applied to the artificial joint prior to or at the same time as the artificial joint is implanted in the subject.

30A. The method according to any one of paragraphs 16A-28A, wherein the nanoscale diamond particles and/or the composition are injected in the subject at or near the artificial joint.

31A. The composition according to any one of paragraphs 1A-15A or the method according to any one of paragraphs 16-30, wherein the nanoscale diamond particles have a zeta potential of about −20 mV to about −50 mV, about −25 mV to about −45 mV, or about −35 mV.

It should be emphasized that the above-described aspects of the present disclosure are merely possible examples of implementations, and are set forth only for a clear understanding of the principles of the disclosure. Many variations and modifications may be made to the above-described aspects of the disclosure without departing substantially from the spirit and principles of the disclosure. All such modifications and variations are intended to be included herein within the scope of this disclosure.

What is claimed is:

1. A composition configuoured to lubricate an artificial joint in a subject in need thereof; the composition comprising:
   (i) a biocompatible carrier fluid; and
   (ii) an effective amount of nanoscale diamond particles dispersed in the biocompatible carrier fluid to lubricate the artificial joint in the subject,
   Wherein the nanoscale diamond particles are present at a concentration of about 0.001 wt % to about 0.25 wt %.

2. The composition according to claim 1, wherein the nanoscale diamond particles are spherical, elliptical, faceted, or a mixture thereof.

3. The composition according to claim 1, wherein the nanoscale diamond particles comprise carbon atoms, and wherein the carbon atoms have an orbital hybridization that is about 95% to about 99% $sp^3$ carbon.

4. The composition according to claim 1, wherein the nanoscale diamond particles are made by a process selected from the group consisting of detonation technique, laser ablation, high-energy ball milling of high-pressure high-temperature (HPHT) diamond microcrystals, plasma-assisted chemical vapor deposition (CVD), autoclave synthesis from supercritical fluids, chlorination of carbides, ion irradiation of graphite, electron irradiation of carbon 'onions', ultrasound cavitation, and a combination thereof.

5. The composition according to claim 1, wherein the nanoscale diamond particles have a volumetric size of about 1 nm to about 20 nm.

6. The composition according to claim 1, wherein the nanoscale diamond particles are carboxylated.

7. The composition according to claim 1, wherein the biocompatible carrier fluid is selected from the group consisting of a simulated body fluid, a synovial fluid, a combination thereof, and mixtures thereof with one or more additional fluids.

8. The composition according to claim 1, wherein the composition is effective to reduce coefficient of friction at the artificial joint by at least 50% as compared to the otherwise same composition except without the nanoscale diamond particles.

9. The composition according to claim 1, wherein the composition is effective to reduce wear at the artificial joint by at least one order of magnitude as compared to the otherwise same composition except without the nanoscale diamond particles.

10. The composition according to claim 1, wherein the composition is effective to reduce bacteria growth by at least 20% as compared to the otherwise same composition except without the nanoscale diamond particles.

11. An artificial joint comprising the composition of claim 1, wherein the artificial joint is made of a material selected from the group consisting of titanium-based alloys, ultra-high-molecular-weight polyethylene, high-density polyethylene, polytetrafluoroethylene, polyoxymethylene, stainless steel, cobalt-based alloys, chromium-based alloys, molybdenum-based alloys, and a combination thereof.

12. The artificial joint according to claim 11, wherein the artificial joint is made of a material selected from the group consisting of Ti—Nb—Ta—Zr, Ti-6Al-7Nb, Ti-6Al-4V, Ti-5Al-2.5Fe, and a combination thereof.

13. The artificial joint according to claim 11, wherein the subject is a mammal.

14. The artificial joint according to claim 11, wherein the artificial joint is selected from the group consisting of hip joint, joint of hand, elbow joint, wrist joint, glenohumeral joint, acromioclavicular joint, sternoclavicular joint, vertebral articulation, temporomandibular joint, sacroiliac joint, knee joint, articulation of foot, and a combination thereof.

15. A method of lubricating an artificial joint in a subject in need thereof, the method comprising: coating an effective amount of nanoscale diamond particles onto the artificial joint to lubricate the artificial joint and/or applying an effective amount of a composition according to claim 1.

16. The method according to claim 15, wherein nanoscale diamond particles are spherical, elliptical, faceted, or a mixture thereof.

17. The method according to claim 15, wherein the nanoscale diamond particles comprise carbon atoms, and
   wherein the carbon atoms have an orbital hybridization that is about 95% to about 99% $sp^3$ carbon.

18. The method according to claim 15, wherein the nanoscale diamond particles are made by a process selected from the group consisting of detonation technique, laser ablation, high-energy ball milling of high-pressure high-temperature (HPHT) diamond microcrystals, plasma-assisted chemical vapor deposition (CVD), autoclave synthesis from supercritical fluids, chlorination of carbides, ion irradiation of graphite, electron irradiation of carbon 'onions', and ultrasound cavitation, and a combination thereof.

19. The method according to claim 15, wherein the nanoscale diamond particles have a volumetric size of about 3 nm, about 4 nm, or about 5 nm.

\* \* \* \* \*